US007074802B2

(12) United States Patent
Doughty et al.

(10) Patent No.: US 7,074,802 B2
(45) Date of Patent: *Jul. 11, 2006

(54) PYRIMIDINE DERIVATIVES AS SELECTIVE INHIBITORS OF COX-2

(75) Inventors: Richard Howard Doughty, deceased, late of Stevenage (GB); by Jennifer Doughty, legal representative, Stevenage (GB); Charles David Hartley, Stevenage (GB); Alan Naylor, Stevenage (GB); Jeremy John Payne, Stevenage (GB); Neil Anthony Pegg, Stevenage (GB)

(73) Assignee: Glaxo Group Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/477,819

(22) PCT Filed: May 23, 2002

(86) PCT No.: PCT/GB02/02414

§ 371 (c)(1),
(2), (4) Date: Apr. 27, 2004

(87) PCT Pub. No.: WO02/096427

PCT Pub. Date: Dec. 5, 2002

(65) Prior Publication Data

US 2005/0032823 A1    Feb. 10, 2005

(30) Foreign Application Priority Data

May 25, 2001 (GB) ................. 0112810.7

(51) Int. Cl.
*C07D 239/42* (2006.01)
*A61K 31/505* (2006.01)

(52) U.S. Cl. ..................... 514/275; 544/332
(58) Field of Classification Search ............ 544/332; 514/275
See application file for complete search history.

(56) References Cited

U.S. PATENT DOCUMENTS

| 3,149,109 | A | 9/1964 | Neustaedter et al. ........ 260/251 |
| 3,592,895 | A | 7/1971 | Hepworth et al. ........... 424/251 |
| 5,474,995 | A | 12/1995 | Ducharme et al. .......... 514/241 |
| 5,760,068 | A | 6/1998 | Talley et al. ................ 514/403 |
| 5,972,986 | A | 10/1999 | Seibert et al. ............... 514/406 |
| 6,020,343 | A | 2/2000 | Belley et al. ............. 514/227.8 |
| 6,153,619 | A | 11/2000 | Wood et al. ................ 514/269 |
| 6,306,866 | B1 | 10/2001 | Wood et al. ................ 514/274 |
| 6,313,072 | B1 | 11/2001 | Scheiblich et al. ......... 504/242 |
| 6,780,869 | B1 | 8/2004 | Green et al. ................ 514/275 |
| 6,780,870 | B1 | 8/2004 | Naylor et al. ............... 514/275 |
| 2003/0013717 | A1* | 1/2003 | Mangel et al. .............. 514/248 |

FOREIGN PATENT DOCUMENTS

| DE | 19909541 | 3/1999 |
| JP | 9241161 | 9/1997 |
| WO | WO 96/07641 | 3/1996 |
| WO | WO 96/24585 | 8/1996 |
| WO | WO 96/41625 | 12/1996 |
| WO | WO 96/41645 | 12/1996 |
| WO | WO/98/03484 | 1/1998 |
| WO | WO 98/16227 | 4/1998 |
| WO | WO/98/24782 | 6/1998 |
| WO | WO 99/01439 | 1/1999 |
| WO | WO/01/38311 | 5/2001 |
| WO | WO/01/58881 | 8/2001 |
| WO | WO/02/18374 | 3/2002 |
| WO | WO/02/096427 | 12/2002 |
| WO | WO/02/096885 | 12/2002 |
| WO | WO/02/096886 | 12/2002 |

OTHER PUBLICATIONS

Simone, J.V., "Oncology: Introduction" Cecil Texbook of Medicine, 20th Edition, vol. 1, pp. 1004-1010, 1996.
Layzer, R.B., "Degenerative Diseases of the Nervous System" Cecil Textbook of Medicine, 20th Edition, vol. 2, pp. 2050-2057, 1996.

(Continued)

*Primary Examiner*—Deepak Rao
(74) *Attorney, Agent, or Firm*—J. Scott Young

(57) ABSTRACT

The invention thus provides the compounds of formula (I)

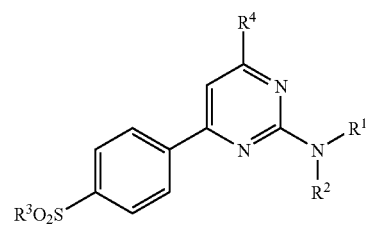

(I)

and pharmaceutically acceptable salts thereof, in which:
$R^1$ and $R^2$ are independently selected from the group consisting of H, $C_{1-6}$alkyl, $C_{2-6}$alkenyl, $C_{3-6}$alkynyl, $C_{3-10}$cycloalkyl$C_{0-6}$alkyl and $C_{4-12}$bridged cycloalkyl;
$R^3$ is selected from the group consisting of $C_{1-6}$alkyl, $NH_2$ and $R^5$CONH;
$R^4$ is selected from the group consisting of $CH_2F$, $CHF_2$, $CF_3CH_2$, $CF_3CHF$ and $CF_3CF_2$; and
$R^5$ is selected from the group consisting of H, $C_{1-6}$alkyl, $C_{1-6}$alkoxy, $C_{1-6}$alkylO$C_{1-6}$alkyl, phenyl, $HO_2CC_{1-6}$alkyl, $C_{1-6}$alkylOCOC$_{1-6}$alkyl, $C_{1-6}$alkylOCO, $H_2NC_{1-6}$alkyl, $C_{1-6}$alkylOCONHC$_{1-6}$alkyl and $C_{1-6}$alkylCONHC$_{1-6}$alkyl.

Compounds of formula (I) are potent and selective inhibitors of COX-2 and are of use in the treatment of the pain, fever, inflammation of a variety of conditions and diseases.

23 Claims, No Drawings

OTHER PUBLICATIONS

Damasio, A.R. "Alzheimer's Disease and Related Dementias" Cecil Textbook of Medicine, 20th Edition, vol. 2, pp. 1992-1996, 1996.

Freston, JW. "Rationalizing Cyclooxygenase (COX) Inhibition for Maximal Efficacy and Minimal Adverse Events & Discussion." PubMed Abstract, Am J Med 107(6A):78S-88S, Discussion 89S), Dec. 1999.

Naesdal, J. et al. "Gastro-Duodenal Protection in an Era of Cyclo-Oxygenase-2-Selective Nonsteroidal Anti-inflammatory Drugs." PubMed Abstract, Eur J Gastroenterol Hepatol, 13(12):1401-1406, Dec. 2001.

Douglas, R.G., Jr. Introduction to Viral Diseases: Cecil Textbook of Medicine, 20th Edition, vol. 2, pp. 1739-1747, 1996.

* cited by examiner

PYRIMIDINE DERIVATIVES AS SELECTIVE INHIBITORS OF COX-2

CROSS REFERENCES TO RELATED APPLICATIONS

This application is a 371 Application of PCT/GB02/02414, filed 23 May 2002, which claims priority to GB Application Serial No. 0112810.7, filed 25 May 2001.

This invention relates to pyrimidine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is largely responsible for the important physiological functions such as maintenance of gastrointestinal integrity and renal blood flow. In contrast the inducible form, COX-2, is believed to be largely responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

The invention thus provides the compounds of formula (I)

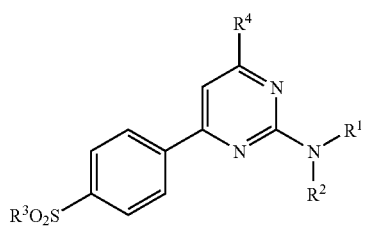

and pharmaceutically acceptable salts thereof, in which:
$R^1$ and $R^2$ are independently selected from the group consisting of H, $C_{1-6}$alkyl, $C_{2-6}$alkenyl, $C_{3-6}$alkynyl, $C_{3-10}$cycloalkyl$C_{0-6}$alkyl and $C_{4-12}$bridged cycloalkyl;
$R^3$ is selected from the group consisting of $C_{1-6}$alkyl, $NH_2$ and $R^5CONH$;
$R^4$ is selected from the group consisting of $CH_2F$, $CHF_2$, $CF_3CH_2$, $CF_3CHF$ and $CF_3CF_2$; and
$R^5$ is selected from the group consisting of H, $C_{1-6}$alkyl, $C_{1-6}$alkoxy, $C_{1-6}$alkylOC$_{1-6}$alkyl, phenyl, $HO_2CC_{1-6}$alkyl, $C_{1-6}$alkylOCOC$_{1-6}$alkyl, $C_{1-6}$alkylOCO$, $H_2NC_{1-6}$alkyl, $C_{1-6}$alkylOCONHC$_{1-6}$alkyl and $C_{1-6}$alkylCONHC$_{1-6}$alkyl.

Suitable pharmaceutically acceptable salts include acid addition salts formed with the amine functionality $NR^1R^2$. Pharmaceutically acceptable salts include those described by Berge, Bighley and Monkhouse, J. Pharm. Sci., 1977, 66, 1–19. Such salts may be formed from inorganic and organic acids. Representative examples thereof include maleic, fumaric, benzoic, ascorbic, pamoic, succinic, bismethylene-salicyclic, methanesulfonic, p-toluenesulfonic, ethanedisulfonic, acetic, propionic, tartaric, salicyclic, citric, gluconic, aspartic, stearic, palmitic, itaconic, glycolic, p-aminobenzoic, glutamic, taurocholic, benzenesulfonic, hydrochloric, hydrobromic, sulfuric, cyclohexylsulfamic, phosphoric and nitric acids.

It will be appreciated that, for pharmaceutical use, the salts referred to above will be the physiologically acceptable salts, but other salts may find use, for example in the preparation of compounds of formula (I) and the physiologically acceptable salts thereof.

The term 'alkyl' as a group or part of a group means a straight or branched chain alkyl group, for example a methyl, ethyl, n-propyl, i-propyl, n-butyl, s-butyl or t-butyl group.

It is to be understood that the present invention encompasses all isomers of the compounds of formula (I) and their pharmaceutically acceptable salts, including all geometric, tautomeric and optical forms, and mixtures thereof (e.g. racemic mixtures).

In one aspect of the invention $R^1$ is H.

In another aspect of the invention $R^2$ is $C_{1-6}$alkyl, such as straight chain $C_{1-6}$alkyl (e.g. n-propyl, n-butyl or n-pentyl).

In another aspect of the invention $R^2$ is a branched chain $C_{3-6}$alkyl, such as s-butyl or t-butyl (e.g. s-butyl).

In another aspect of the invention $R^3$ is $C_{1-6}$alkyl, such as $C_{1-3}$alkyl (e.g. methyl).

In another aspect of the invention $R^4$ is $CH_2F$ or $CF_2H$.

In another aspect of the invention $R^5$ is selected from the group consisting of $C_{1-6}$alkyl (e.g. ethyl), phenyl and aminomethyl.

It is to be understood that the invention covers all combinations of particular aspects of the invention as described hereinabove.

In another aspect the invention provides the following compounds:
N-butyl-4-(fluoromethyl)-6-[4-(methylsulfonyl)phenyl]pyrimidin-2-amine;
N-butyl-4-(difluoromethyl)-6-[4-(methylsulfonyl)phenyl]pyrimidin-2-amine;

and pharmaceutically acceptable salts thereof.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compound of formula (I) may be used for preparing the more pure forms used in pharmaceutical compositions. Although the purity of intermediate compounds of the present invention is less critical, it will be readily understood that the substantially pure form is preferred as for the compounds of formula (I). Preferably, whenever possible, the compounds of the present invention are available in crystalline form.

When some of the compounds of this invention are allowed to crystallise or are recrysallised from organic solvents, solvent of recrystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all the polymorphic forms of the compounds of formula (I).

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by selective inhibition of COX-2. Such conditions and diseases are well known in the art and include rheumatic fever; symptoms associated with influenza or other viral infections, such as the common cold; lower back and neck pain; headache; toothache; sprains and strains; myositis; sympathetically maintained pain; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention are also useful for the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of the invention are also useful for the treatment of other conditions mediated by selective inhibition of COX-2.

For example, the compounds of the invention inhibit cellular and neoplastic transformation and metastatic tumour growth and hence are useful in the treatment of certain cancerous diseases, such as colonic cancer and prostate cancer. The compounds of the invention are also useful in reducing the number of adenomatous colorectal polyps and thus reduce the risk of developing colon cancer. The compounds of the invention are also useful in the treatment of cancer associated with overexpression of HER-2/neu, in particular breast cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention are also useful in the treatment of liver disease, such as inflammatory liver disease, for example chronic viral hepatitis B, chronic viral hepatitis C, alcoholic liver injury, primary biliary cirrhosis, autoimmune hepatitis, nonalcoholic steatohepatitis and liver transplant rejection.

Compounds of the invention inhibit inflammatory processes and therefore are of use in the treatment of asthma, allergic rhinitis and respiratory distress syndrome; gastrointestinal conditions such as inflammatory bowel disease, Crohn's disease, gastritis, irritable bowel syndrome and ulcerative colitis; and the inflammation in such diseases as vascular disease, migraine, periarteritis nodosa, thyroiditis, aplastic anaemia, Hodgkin's disease, scierodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

Compounds of the invention are also useful in the treatment of disorders ameliorated by a gastroprokinetic agent. Disorders ameliorated by gastroprokinetic agents include ileus, for example post-operative ileus and ileus during sepsis; gastroesophageal reflux disease (GORD, or its synonym GERD); gastroparesis, such as diabetic gastroparesis; and other functional bowel disorders, such as non-ulcerative dyspepsia (NUD) and non-cardiac chest pain (NCCP).

According to a further aspect of the invention, we provide a compound of formula (I) or a pharmaceutically acceptable salt thereof for use in human or veterinary medicine.

According to another aspect of the invention, we provide a compound of formula (I) or a pharmaceutically acceptable salt thereof for use in the treatment of a condition which is mediated by COX-2.

According to a further aspect of the invention, we provide a method of treating a human or animal subject suffering from a condition which is mediated by COX-2 which comprises administering to said subject an effective amount of a compound of formula (I) or a pharmaceutically acceptable salt.

According to a further aspect of the invention, we provide a method of treating a human or animal subject suffering from an inflammatory disorder, which method comprises administering to said subject an effective amount of a compound of formula (I) or a pharmaceutically acceptable salt thereof.

According to another aspect of the invention, we provide the use of a compound of formula (I) or a pharmaceutically acceptable salt thereof for the manufacture of a therapeutic agent for the treatment of a condition which is mediated by COX-2.

According to another aspect of)the invention, we provide the use of a compound of formula (I) or a pharmaceutically acceptable salt thereof for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor α; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine. It is to be understood that the present invention covers the use of a compound of formula (I) or a pharmaceutically acceptable salt thereof in combination with one or more other therapeutic agents.

The compounds of formula (I) and their pharmaceutically acceptable salts are conveniently administered in the form of pharmaceutical compositions. Thus, in another aspect of the invention, we provide a pharmaceutical composition comprising a compound of formula (I) or a pharmaceutically acceptable salt thereof adapted for use in human or veterinary medicine. Such compositions may conveniently be presented for use in conventional manner in admixture with one or more physiologically acceptable carriers or excipients.

The compounds of formula (I) and their pharmaceutically acceptable salts may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable salts.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising andlor dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable salt thereof together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) and pharmaceutically acceptable salts thereof may be prepared by any method known in the art for the preparation of compounds of analogous structure.

Compounds of formula (I) and pharmaceutically acceptable salts thereof may be prepared by a process which comprises:

reacting an amine $HNR^1R^2$ of formula (II) or a protected derivative thereof with a compound of formula (III)

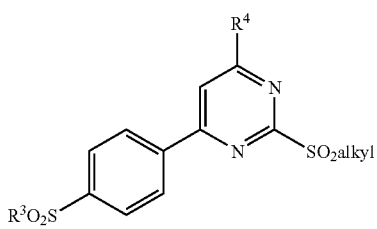

and thereafter and if necessary, interconverting a compound of formula (I) into another compound of formula (I); and/or deprotecting a protected derivative of compound of formula (I).

The overall synthesis of a compound of formula (I) is shown in Scheme 1 below in which, $R^1$ $R^2$ and $R^4$ are as defined in formula (I) above unless otherwise stated, $R^3$ is $C_{1-6}$alkyl; MTBE is methyl t-butyl ether; and alkyl is a straight or branched chain alkyl group, for example a methyl, ethyl, n-propyl, i-propyl, n-butyl, s-butyl or t-butyl group.

Referring to Scheme 1, the treatment of compounds of formula (III) with an amine of formula (II) is conveniently carried out in a solvent, such as nitrile (e.g. methylnitrile) and at elevated temperature (e.g. from about 50° C. to reflux). An excess of the amine may be used in place of the solvent.

Alternatively, the treatment of compounds of formula (III) with an amine of formula (II) is conveniently carried out in a solvent, such as a tertiary amine (e.g. NMP), and at between ambient and elevated temperature (e.g. ambient temperature). Use of, for example, NMP as solvent has the advantage that after completion of the reaction the desired compound of formula (I) may be precipitated from the reaction mixture by the addition of water, allowing for easier isolation and purification.

Conveniently the oxidation shown in Scheme 1 is effected using a monopersulfate compound, such as potassium peroxymonosulfate (known as Oxone™) and the reaction is carried out in a solvent, such as an aqueous alcohol, (e.g. aqueous methanol), and at between −78° C. and ambient temperature.

Alternatively, the oxidation shown in Scheme 1 may be effected using hydrogen peroxide in the presence of catalytic sodium tungstate dihydrate. The reaction may be carried out in a solvent such as acetic acid and at between ambient temperature and reflux (e.g. 50° C.).

Referring to Scheme 1, the cyclisation of diones of formula (VI) to give the corresponding pyrimidines of formula (IV) is conveniently carried out employing a thioronium salt such as a 2-methyl-2-thiopseudourea sulfate and under reflux.

It will be appreciated by those skilled in the art that certain of the procedures described in Scheme 1 for the preparation of compounds of formula (I) or intermediates thereto may not be applicable to some of the possible substituents.

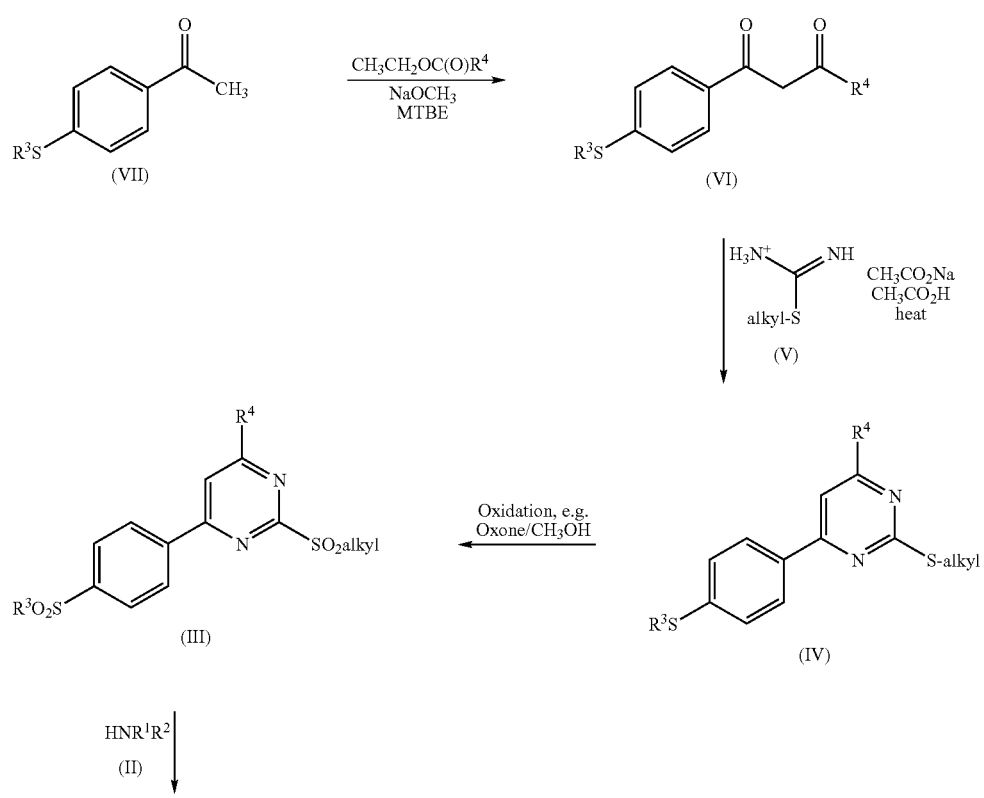

Scheme 1

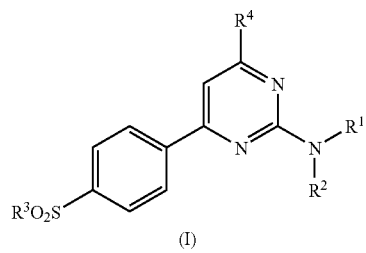

(I)

It will be further appreciated by those skilled in the art that it may be necessary or desirable to carry out the transformations described in Scheme 1 in a different order from that described, or to modify one or more of the transformations, to provide the desired compound of formula (I).

In one variation of Scheme 1, compounds of formula (III) wherein $R^3$ is $C_{1-6}$alkyl or $NH_2$ may be prepared by oxidising a compound of formula (IV)A:

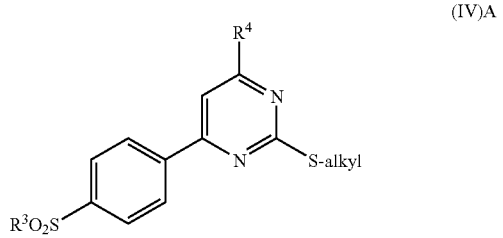

(IV)A under oxidation conditions described hereinabove. Compounds of formula (IV)A may be prepared according to the general procedures of Scheme 1 by employing sulfonyl derivatives in place of the corresponding sulfide compounds of formulae (VI) and (VII).

It will be appreciated by those skilled in the art that compounds of formula (I) may be prepared by interconversion, utilising other compounds of formula (I) as precursors. Suitable interconversions, such as alkylations, are well known to those skilled in the art and are described in many standard organic chemistry texts, such as 'Advanced Organic Chemistry' by Jerry March, fourth edition (Wiley, 1992), incorporated herein by reference. For example, compounds of formula (I) wherein $R^1$ or $R^2$ is $C_{1-6}$alkyl, $C_{2-6}$alkenyl, $C_{3-6}$alkynyl, $C_{3-10}$cycloalkyl$C_{0-6}$alkyl or $C_{4-12}$bridged cycloalkane may be prepared by alkylating the corresponding compound of formula (I) wherein $R^1$ is H.

Acylation of compounds of formula (I) wherein $R^3$ is $NH_2$, to provide compounds of formula (I) wherein $R^3$ is $NHCOR^5$, may be carried out by conventional means, for example by employing conventional acylating agents such as those described in 'Advanced Organic Chemistry', pp 417–424, incorporated herein by reference.

As will be appreciated by those skilled in the art it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See, for example, those described in 'Protective Groups in Organic Synthesis' by Theodora W Green and Peter G M Wuts, second edition, (John Wiley and Sons, 1991), incorporated herein by reference, which also describes methods for the removal of such groups.

Amines of formula (II) are either known compounds or may be prepared by literature methods, such as those described in 'Comprehensive Organic Transformations: a guide to functional group preparations' by Richard Larock (VCH, 1989), incorporated herein by reference.

Thioronium salts of formula (V) are either known compounds or may be prepared by literature methods, such as those described in A H Owens et al, Eur J Med Chem, 1988, 23(3), 295–300, incorporated herein by reference Acetophenones of formula (VII) are either known compounds or may be prepared by conventional chemistry.

Certain intermediates described above are novel compounds, and it is to be understood that all novel intermediates herein form further aspects of the present invention. Compounds of formulae (III) and (IV) are key intermediates and represent a particular aspect of the present invention.

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The Examples that follow illustrate the invention but do not limit the invention in any way.

EXAMPLE 1

N-Butyl-4-(fluoromethyl)-6-[4-(methylsulfonyl)phenyl]pyrimidin-2-amine

LC/MS: retention time 3.38 min; MH+338.3

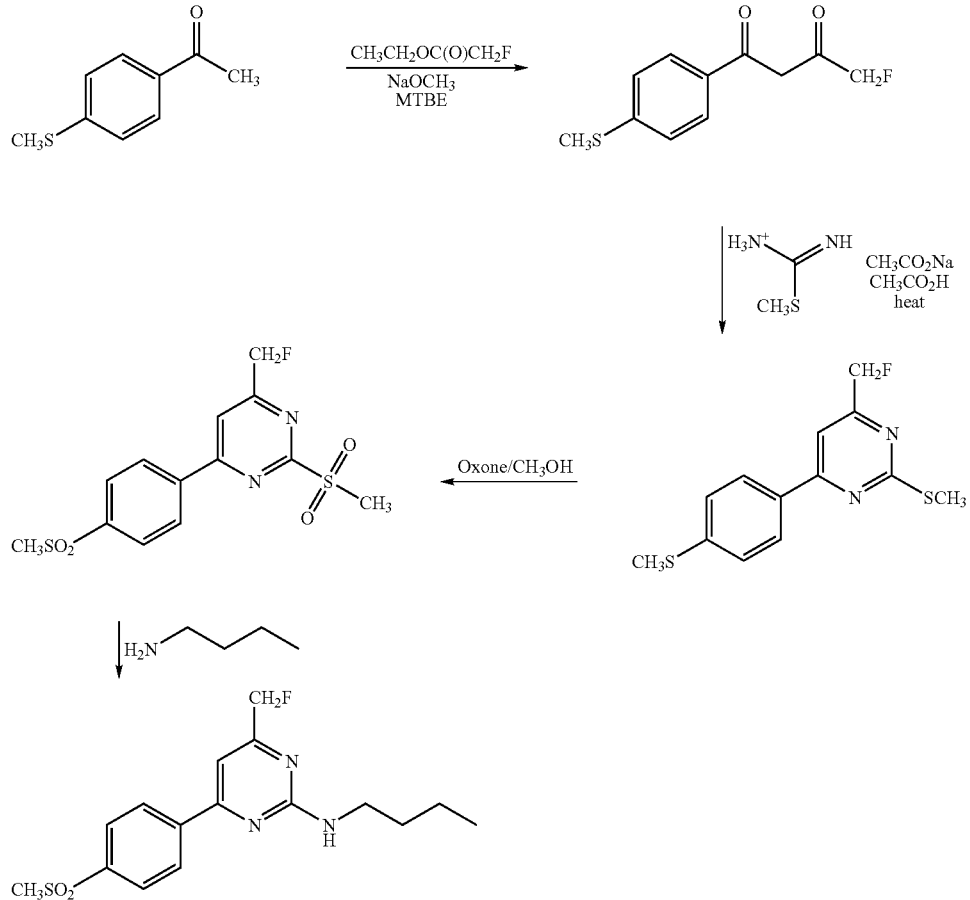

N-butyl-4-(fluoromethyl)-6-[4-(methylsulfonyl)phenyl]pyrimidin-2-amine

EXAMPLE 2

N-butyl-4-(difluoromethyl)-6-[4-(methylsulfonyl)phenyl]pyrimidin-2-amine

Example 2 was prepared in an analogous fashion to Example 1 above, replacing ethyl fluoroacetate with ethyl difluoroacetate in the first stage of the reaction sequence.
LC/MS: retention time 3.48 min; MH+356

Biological Data

Microsomal Assay

Inhibitory activity against microsomal h-COX2 was assessed against a microsomal preparation from baculovirus infected SF9 cells. An aliquot of microsomal preparation was thawed slowly on ice and a 1/40,000 dilution prepared from it into the assay buffer (sterile water, degassed with argon containing 100 mM HEPES (pH 7.4), 10 mM EDTA (pH7.4), 1 mM phenol, 1 mM reduced glutathione, 20 mg/ml gelatin and 0.001 mM Hematin). Once diluted the enzyme solution was then sonicated for 5 seconds (Branson sonicator, setting 4, 1 cm tip) to ensure a homogeneous suspension. 155 µl enzyme solution was then added to each well of a 96-well microtitre plate containing either 5 µl test compound (40× required test concentration) or 5 µl DMSO for controls. Plates were then mixed and incubated at room temperature for 1 hour. Following the incubation period, 40 µl of 0.5 µM arachidonic acid was added to each well to give a final concentration of 0.1 µM. Plates were then mixed and incubated for exactly 10 minutes (room temperature) prior to addition of 25 µl 1M HCl (hydrochloric acid) to each well to stop the reaction. 25 µl of 1M NaOH (sodium hydroxide) was then added to each well to neutralise the solution prior to determination of $PGE_2$ levels by enzyme immunoassay (EIA).

The following $IC_{50}$ values for inhibition of COX-2 and COX-1 were obtained from the microsomal assay for compounds of the invention:

| Example No. | COX-2: IC$_{50}$ (nM) | COX-1: IC$_{50}$ (nM) |
|---|---|---|
| 1 | 761 | >10,000 |
| 2 | 17 | >94,000 |

The invention claimed is:

1. A compound of formula (I)

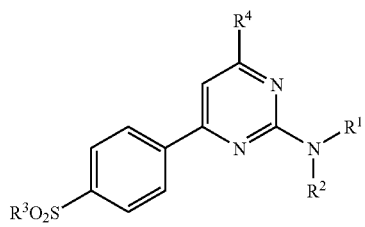

(I)

or a pharmaceutically acceptable salt thereof, in which:

R$^1$ and R$^2$ are independently selected from the group consisting of H, C$_{1-6}$alkyl, C$_{2-6}$alkenyl, C$_{3-6}$alkynyl, C$_{3-10}$cycloalkylC$_{0-6}$alkyl and C$_{4-12}$bridged cycloalkyl;

R$_3$ is selected from the group consisting of C$_{1-6}$alkyl, NH$_2$ and R$^5$CONH;

R$^4$ is selected from the group consisting of CH$_2$F, CHF$_2$, CF$_3$CH$_2$, CF$_3$CHF and CF$_3$CF$_2$; and R$^5$ is selected from the group consisting of H, C$_{1-6}$alkyl, C$_{1-6}$alkoxy, C$_{1-6}$alkylOC$_{1-6}$alkyl, phenyl, HO$_2$CC$_{1-6}$alkyl, C$_{1-6}$alkylOCOC$_{1-6}$alkyl, C$_{1-6}$alkylOCO, H$_2$NC$_{1-6}$alkyl, C$_{1-6}$alkylOCONHC$_{1-6}$alkyl and C$_{1-6}$alkylCONHC$_{1-6}$alkyl.

2. The compound as claimed in claim 1 wherein R$^1$ is H.

3. A compound as claimed in claim 1, wherein R$^2$ is C$_{1-6}$alkyl.

4. A compound as claimed in claim 1 wherein R$^3$ is C$_{1-6}$alkyl.

5. A compound as claimed in claim 1 wherein R$^4$ is CH$_2$F or CHF$_2$.

6. A compound as claimed in claim 1 wherein R$^5$ is selected from the group consisting of C$_{1-6}$alkyl, phenyl and aminomethyl.

7. A compound as claimed in claim 1 wherein R$^2$ is straight chain C$_{1-6}$alkyl or branched chain C$_{3-6}$alkyl.

8. A compound selected from:
N-butyl-4-(fluoromethyl)-6-[4-(methylsulfonyl)phenyl]pyrimidin-2-amine;
N-butyl-4-(difluoromethyl)-6-[4-(methylsulfonyl)phenyl]pyrimidin-2-amine;
and pharmaceutically acceptable salts thereof.

9. A process for the preparation of a compound as defined in claim 1, which comprises:

(A), reacting an amine HNR$^1$R$^2$ of formula (II) or a protected derivative thereof with a compound of formula (III)

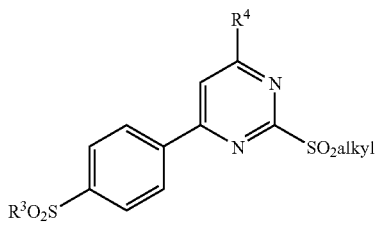

(III)

and thereafter and if necessary, (B), interconverting a compound of formula (I) into another compound of formula (I); and/or (C), deprotecting a protected derivative of compound of formula (I).

10. A pharmaceutical composition comprising a compound as defined in claim 1 in admixture with one or more physiologically acceptable carriers or excipients.

11. A method of treating a subject suffering from acute or chronic pain which comprises administering to said subject an effective amount of a compound as claimed in claim 1.

12. The method according to claim 11 wherein said acute or chronic pain is lower back or neck pain.

13. The method according to claim 11 wherein said acute or chronic pain is neuropathic pain.

14. The method according to claim 11 wherein said acute or chronic pain is non-specific lower back pain.

15. The method according to claim 11 wherein said acute or chronic pain is post-herpetic neuralgia.

16. The method according to claim 11, wherein said subject is a human.

17. A method of treating a subject suffering from dysmenorrhoea which comprises administering to said subject an effective amount of a compound as claimed in claim 1.

18. The method according to claim 17, wherein said subject is a human.

19. A method of treating a subject suffering from arthritis which comprises administering to said subject an effective amount of a compound as defined in claim 1.

20. The method according to claim 19 wherein said arthritis is rheumatoid arthritis.

21. The method according to claim 19 wherein said subject is a human.

22. A method of treating a subject suffering from osteoarthritis which comprises administering to said subject an effective amount of a compound as defined in claim 1.

23. The method according to claim 22 wherein said subject is a human.

* * * * *

UNITED STATES PATENT AND TRADEMARK OFFICE
CERTIFICATE OF CORRECTION

PATENT NO. : 7,074,802 B2 Page 1 of 1
APPLICATION NO. : 10/477819
DATED : July 11, 2006
INVENTOR(S) : Green et al.

It is certified that error appears in the above-identified patent and that said Letters Patent is hereby corrected as shown below:

Title Page
Should read:
item -- (75) Inventors: Richard Howard Green, deceased, --

Signed and Sealed this

Tenth Day of April, 2007

JON W. DUDAS
*Director of the United States Patent and Trademark Office*